United States Patent
Nakae et al.

(10) Patent No.: US 11,604,160 B2
(45) Date of Patent: Mar. 14, 2023

(54) GAS SENSOR

(71) Applicant: DENSO CORPORATION, Kariya (JP)

(72) Inventors: Makoto Nakae, Kariya (JP); Shota Imada, Kariya (JP)

(73) Assignee: DENSO CORPORATION, Kariya (JP)

( * ) Notice: Subject to any disclaimer, the term of this patent is extended or adjusted under 35 U.S.C. 154(b) by 584 days.

(21) Appl. No.: 16/656,959

(22) Filed: Oct. 18, 2019

(65) Prior Publication Data
US 2020/0049653 A1  Feb. 13, 2020

Related U.S. Application Data

(63) Continuation of application No. PCT/JP2018/015747, filed on Apr. 16, 2018.

(30) Foreign Application Priority Data

Apr. 21, 2017 (JP) .............................. JP2017-084568
Feb. 5, 2018 (JP) .............................. JP2018-018540

(51) Int. Cl.
*G01N 27/407* (2006.01)
*G01N 33/00* (2006.01)
(Continued)

(52) U.S. Cl.
CPC ..... *G01N 27/4075* (2013.01); *B01D 53/9454* (2013.01); *F01N 3/10* (2013.01);
(Continued)

(58) Field of Classification Search
CPC .......... G01N 27/4075; G01N 27/4073; G01N 27/409; G01N 33/0036; G01N 27/4062; B01D 53/9454; F01N 3/10; F01N 11/007
See application file for complete search history.

(56) References Cited

U.S. PATENT DOCUMENTS 4,097,353 A * 6/1978 Kishida .............. G01N 27/4075
427/454
4,282,080 A * 8/1981 Muller ................... G01N 27/48
204/412
(Continued)

FOREIGN PATENT DOCUMENTS

JP S61-051557 3/1986
JP H10-082760 3/1998
(Continued)

*Primary Examiner* — Alexander S Noguerola
(74) *Attorney, Agent, or Firm* — Nixon & Vanderhye P.C.

(57) ABSTRACT

A gas sensor includes a sensor element, and the sensor element includes a bottomed tubular solid electrolyte, a detection electrode provided on an outer surface of the solid electrolyte, a reference electrode provided on an inner surface of the solid electrolyte. The detection electrode of the sensor element includes a detection electrode section provided at a position on a tip side of an axial direction, an attachment electrode section provided at a position on a base end side of the axial direction, and a lead electrode section provided at a position where the detection electrode section is connected to the attachment electrode section. An insulating layer is provided between a tube of the solid electrolyte and each of the attachment electrode section and the lead electrode section.

11 Claims, 14 Drawing Sheets

(51) Int. Cl.
  *G01N 27/409* (2006.01)
  *F01N 11/00* (2006.01)
  *B01D 53/94* (2006.01)
  *F01N 3/10* (2006.01)
  *G01N 27/41* (2006.01)

(52) U.S. Cl.
  CPC ......... *F01N 11/007* (2013.01); *G01N 27/409* (2013.01); *G01N 27/4073* (2013.01); *G01N 27/4077* (2013.01); *G01N 27/41* (2013.01); *G01N 33/0016* (2013.01); *G01N 33/0036* (2013.01); *F01N 2560/025* (2013.01)

(56) References Cited

U.S. PATENT DOCUMENTS

| | | | | |
|---|---|---|---|---|
| 4,402,820 | A * | 9/1983 | Sano | G01N 27/4077 204/429 |
| 5,088,281 | A * | 2/1992 | Izutani | F01N 11/007 60/276 |
| 5,169,513 | A * | 12/1992 | Mase | B32B 18/00 427/126.3 |
| 5,393,397 | A | 2/1995 | Fukaya et al. | |
| 5,556,526 | A * | 9/1996 | Fukaya | G01N 27/407 204/426 |
| 5,670,032 | A * | 9/1997 | Friese | G01N 27/407 204/424 |
| 6,354,134 | B1 * | 3/2002 | Katafuchi | G01N 27/4075 73/23.32 |
| 2006/0220159 | A1 * | 10/2006 | Matsuo | G01N 27/407 257/414 |
| 2009/0014330 | A1 | 1/2009 | Sugaya et al. | |
| 2010/0006433 | A1 | 1/2010 | Yasuda et al. | |
| 2017/0131229 | A1 | 5/2017 | Iwamoto | |

FOREIGN PATENT DOCUMENTS

| | | |
|---|---|---|
| JP | 2009-281727 | 12/2009 |
| JP | 2014/178303 | 9/2014 |

* cited by examiner

GAS SENSOR

CROSS-REFERENCE TO RELATED APPLICATION

This application is a U.S. application under 35 U.S.C. 111(a) and 363 that claims the benefit under 35 U.S.C. 120 from International Application No. PCT/JP2018/015747 filed on Apr. 16, 2018, the entire contents of which are incorporated herein by reference. This application is also based on Japanese Patent Application No. 2017-084568 filed on Apr. 21, 2017 and Japanese Patent Application No. 2018-018540 filed on Feb. 5, 2018, the contents of which are incorporated herein by reference.

BACKGROUND

Technical Field

The present disclosure relates to a gas sensor.

Background Art

An oxygen sensor, in which an insulating layer composed of an insulator is provided between a solid electrolyte and a lead section of a detection electrode, and the insulating layer defines an area of the detection electrode that functions during gas detection is known.

SUMMARY

An aspect of the present disclosure is a gas sensor including a sensor element, wherein: the sensor element includes a solid electrolyte that has a bottomed tubular shape, a detection electrode, and a reference electrode; the detection electrode includes a detection electrode section, an attachment electrode section that is in contact with a terminal metal fitting, and a lead electrode section connecting the detection electrode section and the attachment electrode section; and an insulating layer that insulates the solid electrolyte from the attachment electrode section and the lead electrode section is provided between the tube of the solid electrolyte and each of the attachment electrode section and the lead electrode section.

BRIEF DESCRIPTION OF THE DRAWINGS

Objects, features, advantages, and the like of the present disclosure will be more clarified by the following detailed description with reference to the accompanying drawings. The drawings of the present disclosure are as follows.

DETAILED DESCRIPTION OF THE PREFERRED EMBODIMENTS

Figure 1:
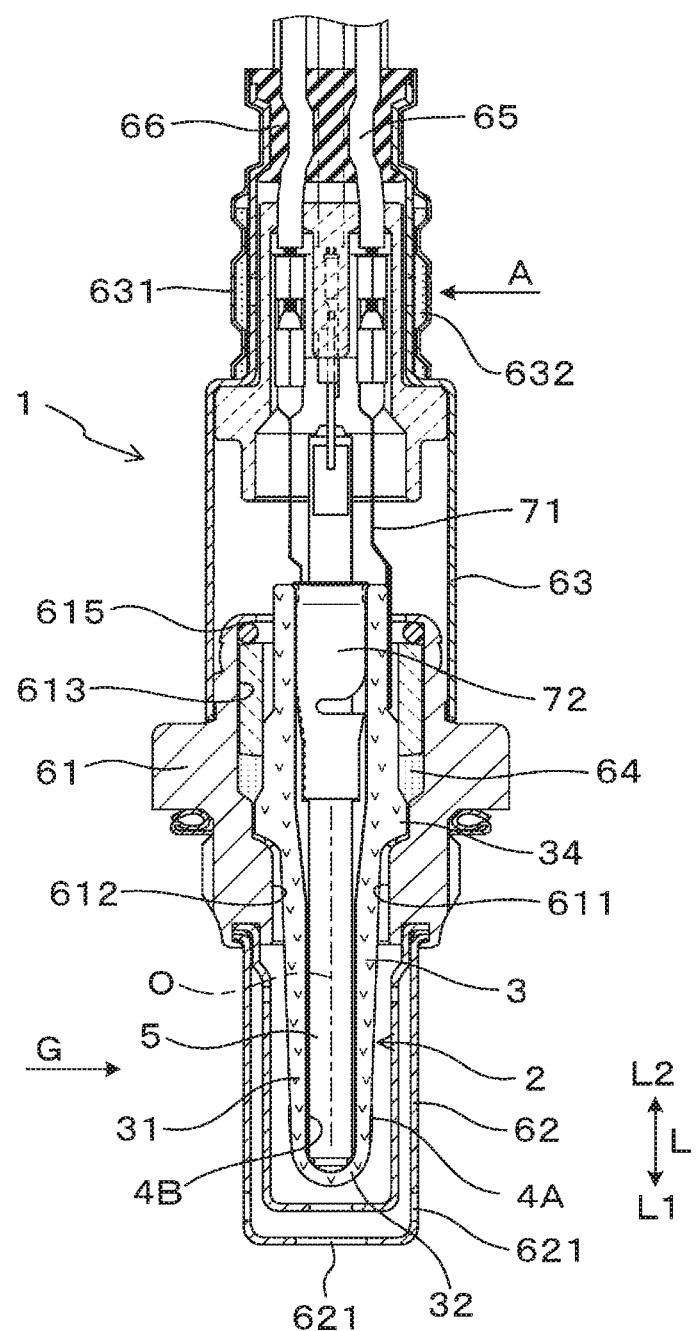
FIG. 1 is an explanatory view showing a cross section of a gas sensor, according to Embodiment 1.

Preferred embodiments of the above-described gas sensor will be described with reference to the drawings.

The inventor of the present disclosure has studied a gas sensor capable of improving accuracy of gas detection by preventing a leakage current from being generated between an attachment electrode section of a detection electrode and a reference electrode.

A gas sensor arranged in an exhaust pipe of an internal combustion engine uses exhaust gas flowing in the exhaust pipe as detection gas (measurement gas) and detects gas, for example, on the basis of a difference in oxygen concentration between the detection gas and reference gas such as air. For example, the gas sensor is used as an oxygen sensor that detects whether an air-fuel ratio of the internal combustion engine obtained from composition of the exhaust gas is on a fuel rich side or on a fuel lean side with respect to a theoretical air-fuel ratio or used as an air-fuel ratio sensor that quantitatively detects an air-fuel ratio of the internal combustion engine obtained from the exhaust gas.

The gas sensor includes a bottomed tubular sensor element in which electrodes are arranged on an inner surface and an outer surface of a bottomed tubular solid electrolyte or a plate-shaped sensor element in which electrodes are arranged on both surfaces of a plate-shaped solid electrolyte. When the gas sensor is used as the oxygen sensor, on the basis of a difference in oxygen concentration between the detection gas and the reference gas, the gas sensor detects an electromotive force generated between the pair of electrodes through the solid electrolyte. When the gas sensor is used as the air-fuel ratio sensor, a voltage is applied between the pair of electrodes, and on the basis of oxygen concentration of the detection gas, the gas sensor detects an electric current flowing between the pair of electrodes through the solid electrolyte.

In the bottomed tubular sensor element, in many cases, a detection electrode exposed to the detection gas is formed to include a detection section and a lead section. The detection section is formed on an entire periphery of a tip side portion of the solid electrolyte and is heated to a target temperature by a heating section of a heater. The lead section is led from the detection section toward a base end side. It has been known that an insulating layer is provided between the lead section and the solid electrolyte so that movement of oxygen through the solid electrolyte occurs only in the detection section.

As a result of intensive studies, the inventors have found that in an environment where a base end side portion of the sensor element reaches a high temperature of 400° C. or more, even when the detection gas has a composition that is supposed to allow a sensor output of the gas sensor to be an output at the theoretical air-fuel ratio, in some cases, deviation occurs in the sensor output and the sensor output fails to be an output corresponding to the theoretical air-fuel ratio. The inventors have found that this is because when the base end side portion of the sensor element has reached a high temperature, the solid electrolyte, the lead section of the detection electrode, and a reference electrode at the base end side portion of the sensor element are activated, and thus oxygen in the reference gas such as air that is present at the base end side portion of the sensor element moves through the solid electrolyte, so that a leakage current is generated between the lead section of the detection electrode and the reference electrode. It has been found that in particular, the leakage current is generated at a portion of the lead section of the detection electrode to which a terminal metal fitting is attached.

In conventional techniques such as disclosed in JP 6-201641 A, the insulating layer is provided at a portion of the detection electrode exposed to the detection gas or at the lead section. However, while the tip side portion of the sensor element is exposed to the detection gas, the base end side portion of the sensor element is fixed to a housing and thus is not exposed to the detection gas. The insulating layer of Patent Literature 1 is provided to define the area of the detection electrode that functions during gas detection. Accordingly, the insulating layer is not designed to be provided at a base end side portion of the lead section which is not exposed to the detection gas and to which the terminal metal fitting is attached.

The present disclosure is to provide a gas sensor capable of improving accuracy of gas detection by preventing a leakage current from being generated between an attachment electrode section of a detection electrode and a reference electrode.

An aspect of the present disclosure is a gas sensor including a sensor element, wherein: the sensor element includes a solid electrolyte that has a bottomed tubular shape and in which a tip portion of a tube having a tubular shape thereof is blocked by a bottom having a curved surface, a detection electrode that is provided at least on an outer surface of the tube and is exposed to detection gas guided to an outside of the solid electrolyte, and a reference electrode that is provided at least on an inner surface of the tube and is exposed to reference gas guided to an inside of the solid electrolyte; the detection electrode includes a detection electrode section that is provided on an entire periphery or a part in a circumferential direction around a center axis of the tube at a position on a tip side of an axial direction along the center axis, an attachment electrode section that is provided on an entire periphery or a part in the circumferential direction of the tube at a position on a base end side of the axial direction and is in contact with a terminal metal fitting attached to an outer periphery of the tube, and a lead electrode section that is provided on a part in the circumferential direction of the tube at a position where the detection electrode section is connected to the attachment electrode section and that is formed in a formation region in the circumferential direction smaller than a formation region in the circumferential direction of the attachment electrode section; and an insulating layer that insulates the solid electrolyte from the attachment electrode section and the lead electrode section is provided between the tube of the solid electrolyte and each of the attachment electrode section and the lead electrode section.

In the gas sensor, the insulating layer is provided not only between the lead electrode section of the detection electrode and the solid electrolyte but also between the attachment electrode section of the detection electrode to which the terminal metal fitting is attached and the solid electrolyte. Thus, when a base end side portion of the sensor element is heated to a high temperature of 400° C. or more, it is possible to prevent a leakage current being generated between the attachment electrode section of the detection electrode and the reference electrode due to activation of the solid electrolyte and movement of oxygen in the reference gas in contact with the base end side portion of the sensor element.

Accordingly, in a case where the gas sensor is used as an air-fuel ratio sensor, even when the base end side portion of the sensor element is exposed to a high temperature environment of 400° C. or more, it is possible to prevent an offset current from being included in an output current as a sensor output at an air-fuel ratio close to the theoretical air-fuel ratio. Furthermore, in a case where the gas sensor is used as an oxygen sensor, even when the base end side portion of the sensor element is exposed to a high temperature environment of 400° C. or more, it is possible to prevent an error voltage from being included in an output voltage as the sensor output.

Therefore, the gas sensor can improve accuracy of gas detection by preventing a leakage current from being generated between the attachment electrode section of the detection electrode and the reference electrode.

Reference signs in parentheses for components shown in an aspect of the present disclosure indicate a correspondence relationship with reference signs in the drawings of embodiments, but do not limit the components only to the components of the embodiments.

Embodiment 1

Figure 2:
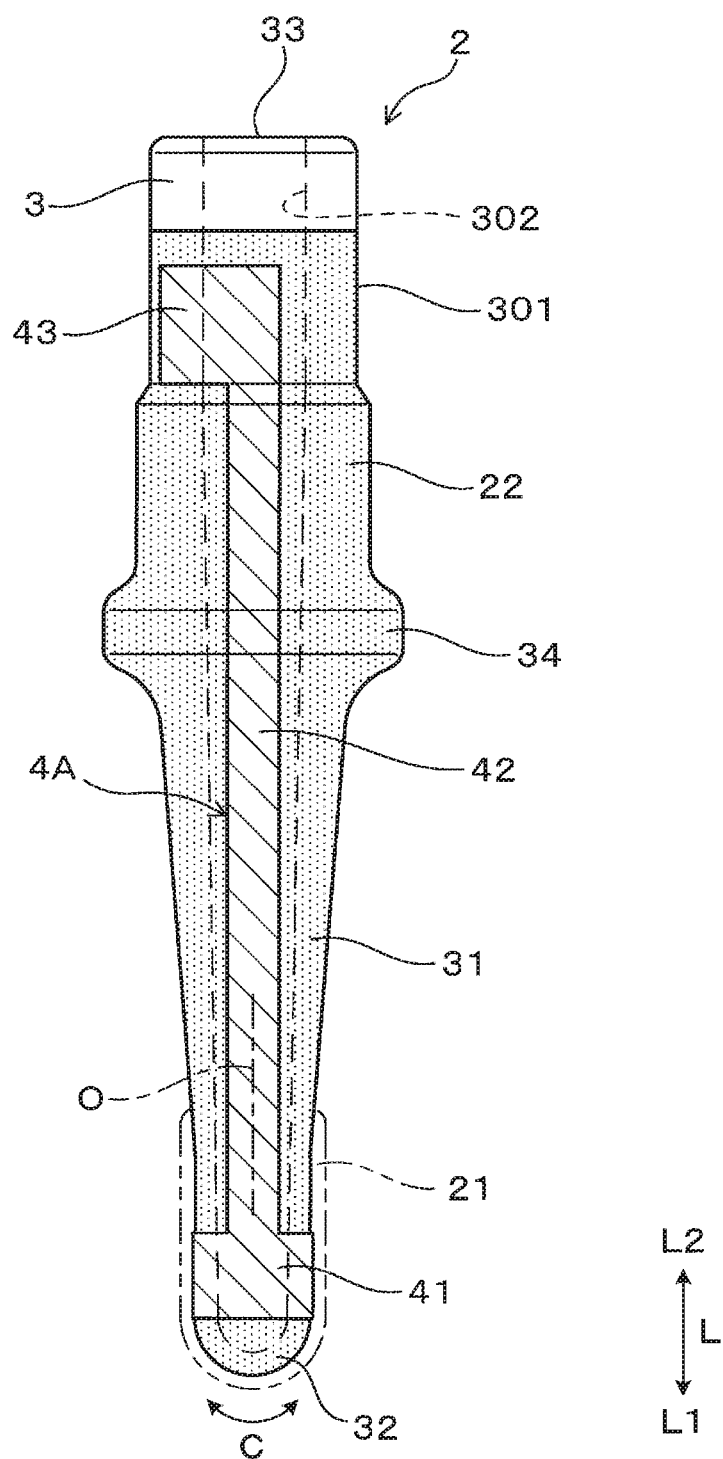
FIG. 2 is an explanatory view showing a formation state of a detection electrode of a sensor element, according to Embodiment 1.
Figure 3:
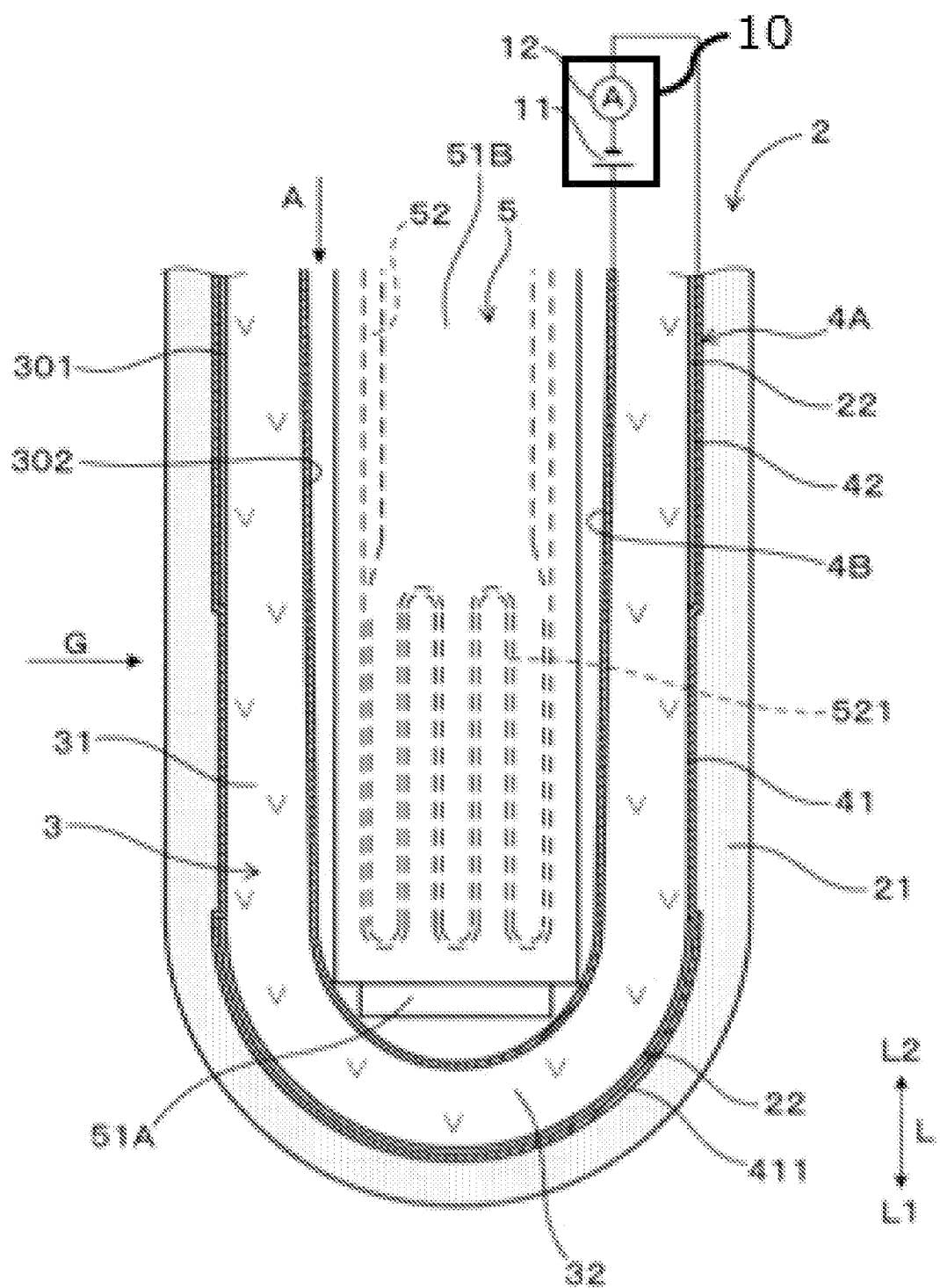
FIG. 3 is an explanatory view showing a cross section of a tip portion of the sensor element, according to Embodiment 1.

As shown in FIGS. 1 to 3, a gas sensor 1 of the present embodiment includes a sensor element 2, and the sensor element 2 includes a solid electrolyte 3 having a bottomed tubular shape, a detection electrode 4A, and a reference electrode 4B. The solid electrolyte 3 has ionic conductivity at an activation temperature, and has a tube 31 that has a tubular shape and a bottom 32 that has a curved surface and blocks a tip portion of the tube 31. The detection electrode 4A is an electrode that is provided on an outer surface 301 of the tube 31 and is exposed to detection gas G guided to an outside of the solid electrolyte 3. The reference electrode 4B is an electrode that is provided on an inner surface 302 of the tube 31 and the bottom 32 and is exposed to reference gas A guided to an inside of the solid electrolyte 3.

The detection electrode 4A includes a detection electrode section 41, an attachment electrode section 43, and a lead electrode section 42. As shown in FIG. 2, the detection electrode section 41 is provided on an entire periphery in a circumferential direction C around a center axis O of the tube 31 at a position on a tip side L1 of an axial direction L along the center axis O. As shown in FIGS. 1 and 2, the attachment electrode section 43 is provided on a part in the circumferential direction C of the tube 31 at a position on a base end side L2 of the axial direction L, and is in contact with a terminal metal fitting 71 attached to an outer periphery of the tube 31. As shown in FIG. 2, the lead electrode section 42 is provided on a part in the circumferential direction C of the tube 31 at a position where the detection electrode section 41 is connected to the attachment electrode section 43, and is formed in a formation region in the circumferential direction C smaller than a formation region in the circumferential direction C of the attachment electrode section 43.

As shown in FIGS. 2 and 3, between the tube 31 of the solid electrolyte 3 and each of the attachment electrode section 43 and the lead electrode section 42, an insulating layer 22 that insulates the solid electrolyte 3 from the attachment electrode section 43 and the lead electrode section 42 is provided. In FIGS. 2, 5, 6, and 8, in order to facilitate understanding, the detection electrode 4A is indicated by diagonal hatching, and a portion where the insulating layer 22 is exposed on a surface is indicated by grating hatching.

Figure 8:
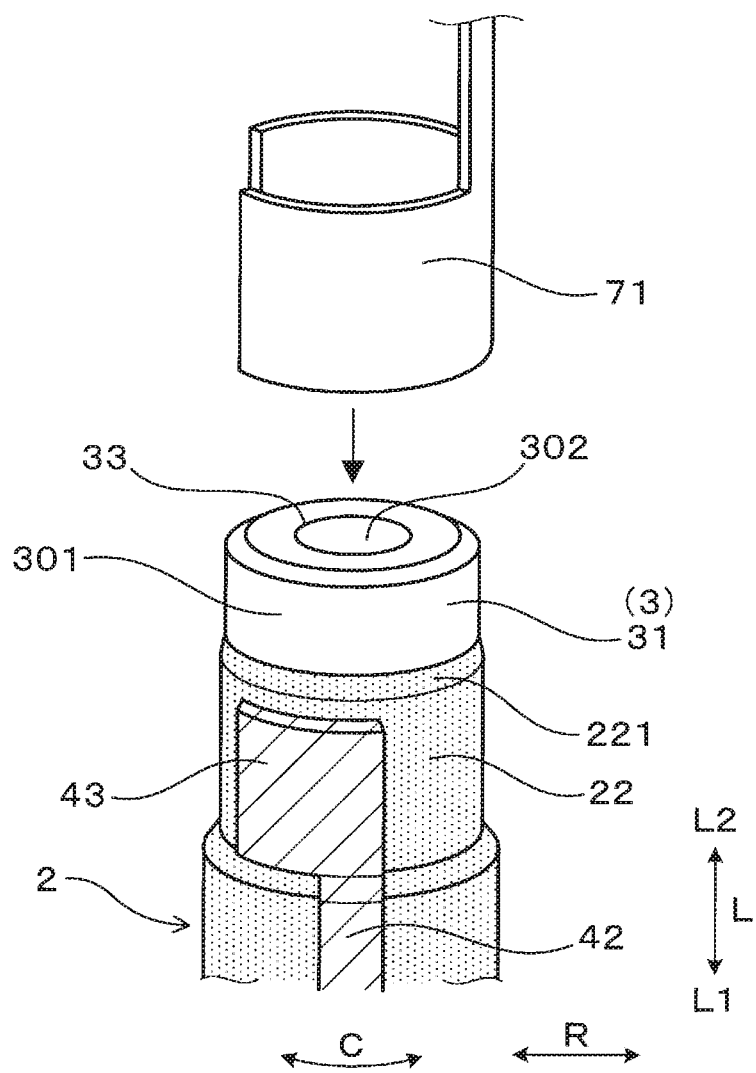
FIG. 8 is a perspective view showing a terminal metal fitting to be attached to the sensor element, according to Embodiment 2.

As shown in FIG. 8, in the sensor element 2 and the gas sensor 1 of Embodiments 1 and 2, a direction along the center axis O of the sensor element 2 is referred to as axial direction L, a direction around the center axis O of the sensor element 2 is referred to as circumferential direction C, and a direction radiating from the center axis O of the sensor element 2 is referred to as radial direction R. Furthermore, in the sensor element 2 and the gas sensor 1, a side on which the bottom 32 of the sensor element 2 is provided is referred to as tip side L1, and a side opposite to the tip side L1 is referred to as base end side L2.

The gas sensor 1 of the present embodiment will be described in detail below.

(Internal Combustion Engine 8)

Figure 4:
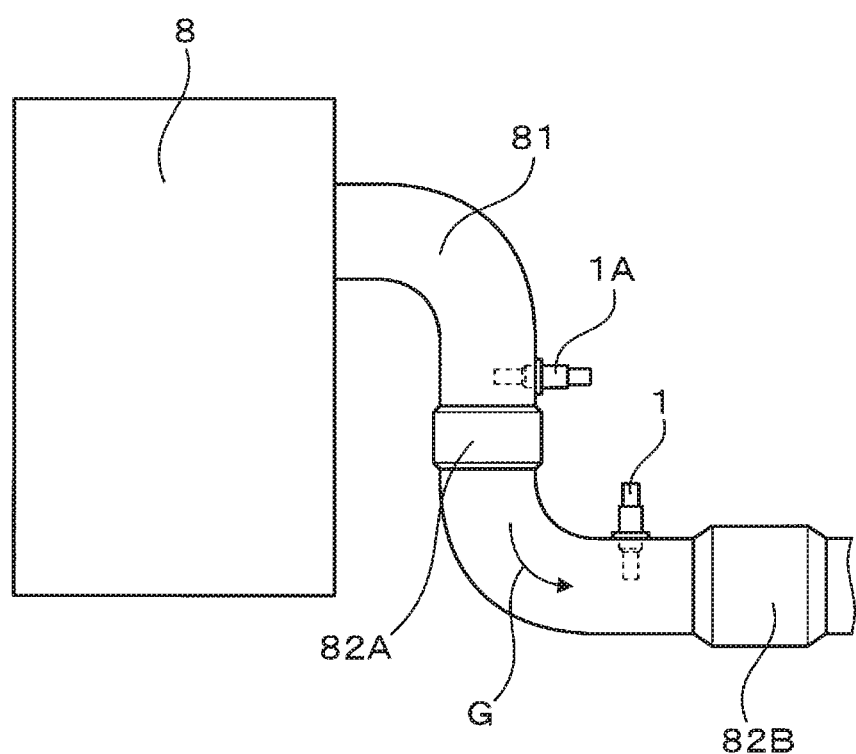
FIG. 4 is an explanatory view showing a state in which the gas sensor is arranged in an exhaust pipe of an internal combustion engine, according to Embodiment 1.

As shown in FIG. 4, the gas sensor 1 is arranged in an exhaust pipe 81 in which exhaust gas discharged from an internal combustion engine (engine) 8 of a vehicle flows. The gas sensor 1 detects gas by using the exhaust gas flowing in the exhaust pipe 81 as the detection gas G and using air as the reference gas A. The gas sensor 1 of the present embodiment is used as an air-fuel ratio sensor that obtains an air-fuel ratio of the internal combustion engine 8 obtained from composition of the exhaust gas. The air-fuel ratio sensor can quantitatively and continuously detect the air-fuel ratio from a fuel rich state in which a ratio of fuel to air is greater than a theoretical air-fuel ratio to a fuel lean state in which the ratio of fuel to air is smaller than the theoretical air-fuel ratio.

As shown in FIG. 3, in the air-fuel ratio sensor, a voltage application circuit 11 applies a predetermined voltage for exhibiting a limiting current characteristic between the detection electrode 4A that is provided on one surface of the solid electrolyte 3 and is exposed to the detection gas G and the reference electrode 4B that is provided on the other surface of the solid electrolyte 3 and is exposed to the reference gas A. While the voltage is applied, a current detection circuit 12 detects a limiting current generated between the detection electrode 4A and the reference electrode 4B through the solid electrolyte 3. In other words, when a change occurs in oxygen concentration of the exhaust gas as the detection gas G, a change occurs in movement amount and movement direction of oxygen ions ($O^{2-}$) between the detection electrode 4A and the reference electrode 4B, and the air-fuel ratio on the fuel rich side and the fuel lean side is quantitatively detected in a predetermined detection range. As shown in FIG. 3, the voltage application circuit 11 and the current detection circuit 12 are constructed in a control unit 10 such as a sensor control unit.

In the air-fuel ratio sensor, since the voltage is applied between the detection electrode 4A and the reference electrode 4B, when the air-fuel ratio is on the fuel lean side, oxygen ions ($O^{2-}$) move from the detection electrode 4A to the reference electrode 4B through the solid electrolyte 3. On the other hand, when the air-fuel ratio is on the fuel rich side, due to a chemical reaction of unburned gas in the detection electrode 4A, oxygen ions ($O^{2-}$) move from the reference electrode 4B to the detection electrode 4A through the solid electrolyte 3.

Figure 5:
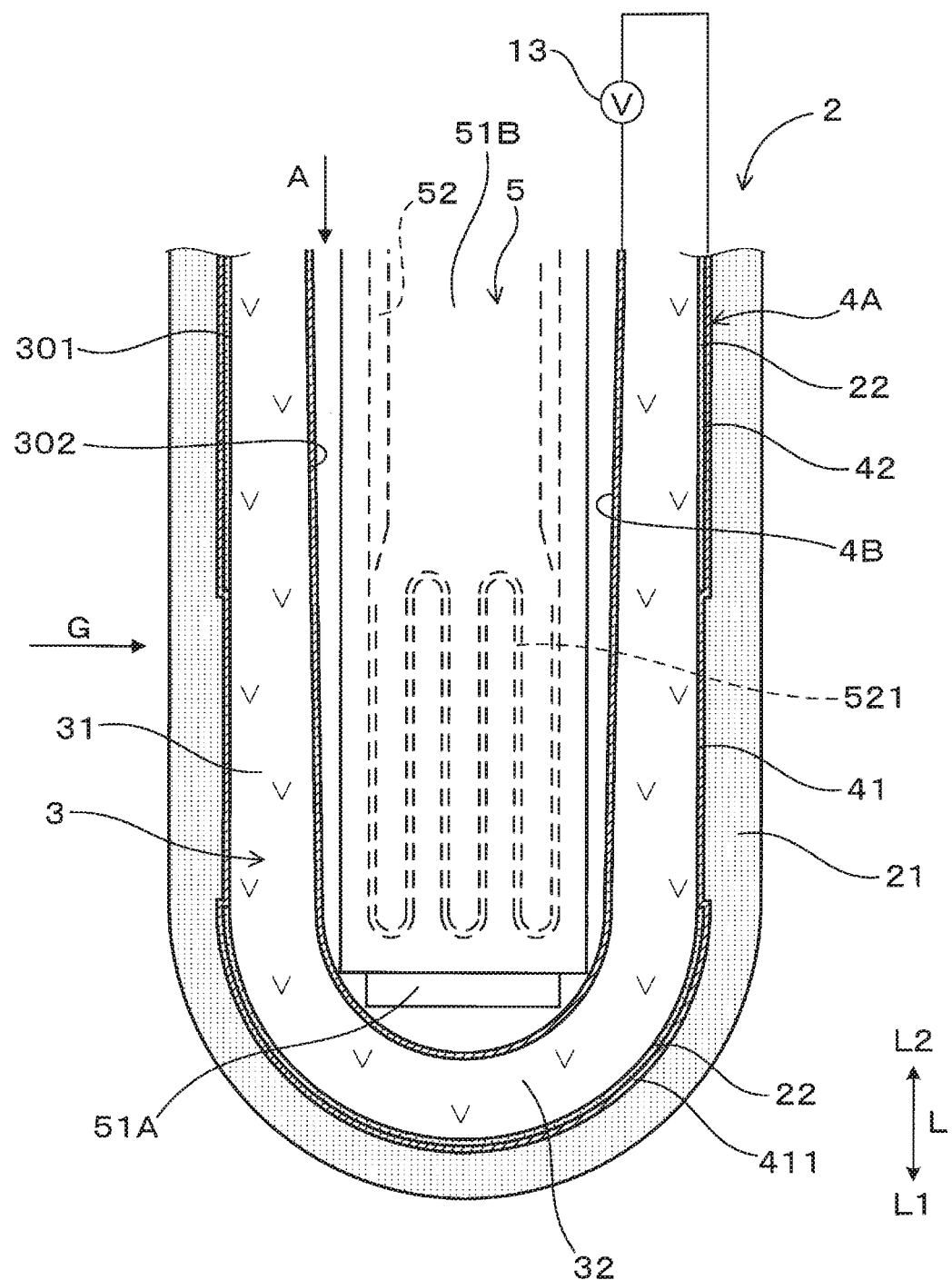
FIG. 5 is an explanatory view showing a cross section of a tip portion of the sensor element used in another detection method, according to Embodiment 1.

As shown in FIG. 5, the gas sensor 1 can also be used as an oxygen sensor that determines by ON/OFF whether the air-fuel ratio of the internal combustion engine 8 obtained from the composition of the exhaust gas is on the fuel rich side or on the fuel lean side. In the oxygen sensor, on the basis of a difference in oxygen concentration between air as the reference gas A in contact with the reference electrode 4B and exhaust gas as the detection gas G in contact with the detection electrode 4A, an electromotive force detection circuit 13 detects an electromotive force generated between the detection electrode 4A and the reference electrode 4B through the solid electrolyte 3. The electromotive force detection circuit 13 is formed in the sensor control unit. Furthermore, on the basis of the electromotive force generated between the detection electrode 4A and the reference electrode 4B, the oxygen sensor can also quantitatively detect oxygen concentration of the exhaust gas.

The gas sensor 1 is used to maintain the air-fuel ratio of the internal combustion engine 8 to be close to the theoretical air-fuel ratio at which catalytic activity of a three-way catalyst arranged in the exhaust pipe 81 is effectively exhibited. The gas sensor 1 may be arranged at a position on an upstream side or a downstream side of a flow of the exhaust gas from an arrangement position of the three-way catalyst in the exhaust pipe 81. In particular, the gas sensor 1 of the present embodiment may be arranged at the position on the downstream side in the exhaust pipe 81 at which the exhaust gas has a lower temperature.

As shown in FIG. 4, two catalysts 82A and 82B arranged in a direction of flow of the exhaust gas are arranged in the exhaust pipe 81 of the present embodiment. The two catalysts 82A and 82B are an upstream-side catalyst 82A (also referred to as S/C (Start Converter) catalyst) located on the upstream side and a downstream-side catalyst 82B (also referred to as U/F (Under Floor) catalyst) located on the downstream side from the upstream-side catalyst 82A. The gas sensor 1 of the present embodiment is arranged at a position that is on the downstream side of the flow of the exhaust gas from the upstream-side catalyst 82A in the exhaust pipe 81 and on the upstream side of the flow of the exhaust gas from the downstream-side catalyst 82B in the exhaust pipe 81. In other words, the gas sensor 1 of the present embodiment is arranged at a position between the upstream-side catalyst 82A and the downstream-side catalyst 82B in the direction of flow of the exhaust gas in the exhaust pipe 81.

Furthermore, another gas sensor 1A is arranged at a position on the upstream side from the upstream-side catalyst 82A in the exhaust pipe 81. The gas sensor 1A functions as the air-fuel ratio sensor. The two gas sensors 1 and 1A are used to detect an air-fuel ratio of the exhaust gas. By using the air-fuel ratio received from the two gas sensors 1 and 1A, an ECU (engine control unit) adjusts a degree of opening of a fuel injection valve in an intake pipe to control the air-fuel ratio of the internal combustion engine 8.

The gas sensor 1 of the present embodiment may be arranged at a position on the upstream side from the upstream-side catalyst 82A in the exhaust pipe 81. In the exhaust pipe 81, typically, the air-fuel ratio sensor is arranged at a position on the upstream side from the upstream-side catalyst 82A and the oxygen sensor is arranged at a position on the downstream side from the upstream-side catalyst 82A.

In particular, when the gas sensor 1 is arranged at a more downstream position in the exhaust pipe 81, the exhaust gas in contact with the gas sensor 1 has a lower temperature, and thus condensed water is more likely to collide with the gas sensor 1. The sensor element 2 of the present embodiment includes the solid electrolyte 3 having a bottomed tubular shape (cup shape), and this effectively prevents water-induced cracking caused by the condensed water in the exhaust pipe 81.

(Sensor Element 2)

As shown in FIGS. 2 and 3, the solid electrolyte 3 of the sensor element 2 contains zirconia as a main component and is composed of stabilized zirconia or partially stabilized zirconia obtained by replacing part of zirconia with a rare earth metal element or an alkaline earth metal element. The solid electrolyte 3 may be composed of yttria stabilized zirconia or yttria partially stabilized zirconia. At a predetermined activation temperature, the solid electrolyte 3 has ionic conductivity that allows oxygen ions ($O^{2-}$) to be conducted. The detection electrode 4A and the reference electrode 4B contain platinum as noble metal that exhibits catalytic activity for oxygen.

The bottom 32 of the solid electrolyte 3 has a hemispherical surface, and the tube 31 of the solid electrolyte 3 has a cylindrical shape. An opening 33 that allows the reference gas A to flow into an inside of the solid electrolyte 3 is formed at a position on a side opposite to the bottom 32 in the axial direction L of the solid electrolyte 3. An outer diameter of each portion in the axial direction L of the tube 31 appropriately varies in consideration of attachment to a housing 61.

At a tip portion of the sensor element 2, a protective layer 21 composed of porous ceramics is provided to cover at least an entire portion of the detection electrode section 41 of the detection electrode 4A. The protective layer 21 of the air-fuel ratio sensor of the present embodiment has a function as a diffusion resistance layer that limits diffusion of the exhaust gas as the detection gas G. When a predetermined voltage is applied between the detection electrode 4A and the reference electrode 4B, a flow rate of the detection gas G passing through the protective layer 21 is limited, and a sensor output according to oxygen concentration of the detection gas G is obtained. The protective layer 21 also has a function of preventing the detection electrode 4A from being poisoned or wetted with water. Furthermore, a porous layer for preventing the detection electrode 4A from being poisoned or wetted with water may be provided outside the protective layer 21 as the diffusion resistance layer.

When the gas sensor 1 is used as the oxygen sensor, the protective layer 21 mainly has a function of preventing the detection electrode 4A from being poisoned or wetted with water. In this case, the protective layer 21 may be formed of a plurality of layers composed of porous materials different in pore rate, composition, or the like.

As shown in FIGS. 1 and 3, the reference electrode 4B is provided on an entire portion of the inner surface 302 of the solid electrolyte 3. An inner terminal metal fitting 72 is attached to a portion on the base end side L2 of the inner surface 302 of the solid electrolyte 3 so that the inner terminal metal fitting 72 is in contact with a portion on the base end side L2 of the reference electrode 4B. Since the gas sensor 1 of the present embodiment is used as the air-fuel ratio sensor, a voltage applied between the reference electrode 4B and the detection electrode 4A causes the reference electrode 4B and the inner terminal metal fitting 72 to be on a positive side and the detection electrode 4A and the terminal metal fitting 71 to be on a negative side.

Similarly to the detection electrode 4A, the reference electrode 4B may be designed to be a partial electrode and constituted by a detection electrode section located at an endmost position on the tip side L1, an attachment electrode section located at an endmost position on the base end side L2, and a lead electrode section connecting the detection electrode section to the attachment electrode section.

The detection electrode section 41 of the detection electrode 4A is a portion of the detection electrode 4A that actually performs gas detection such as air-fuel ratio detection. In other words, in the detection electrode 4A, only the detection electrode section 41 is provided directly on the outer surface 301 of the solid electrolyte 3 without the insulating layer 22 interposed therebetween. In order to stabilize accuracy of gas detection, in other words, in order to reduce variations in the output of the gas sensor 1, an area of the detection electrode section 41 is defined in the sensor element 2. The detection electrode section 41 is heated to a target temperature by a heater 5 arranged inside the solid electrolyte 3 of the sensor element 2.

The lead electrode section 42 of the detection electrode 4A is formed at a single position in the circumferential direction C on the solid electrolyte 3. The lead electrode section 42 is formed parallel to the center axis O of the tube 31 of the solid electrolyte 3 and the axial direction L. In other words, both side ends in the circumferential direction C of the lead electrode section 42 are parallel to the axial direction L.

The attachment electrode section 43 of the detection electrode 4A is formed in the circumferential direction C at a position on the base end side L2 on the outer surface 301 of the solid electrolyte 3. The attachment electrode section 43 of the present embodiment is formed only on a part in the circumferential direction C of the outer surface 301 of the solid electrolyte 3.

As shown in FIG. 3, the insulating layer 22 provided on the outer surface 301 of the sensor element 2 is not provided between the tube 31 and the detection electrode section 41. The insulating layer 22 is provided at an entire portion of the bottom 32, an entire portion between the tube 31 and the lead electrode section 42, and an entire portion between the tube 31 and the attachment electrode section 43. The attachment electrode section 43 of the present embodiment is not provided at a position of a base end of the outer surface 301 of the sensor element 2. The attachment electrode section 43 may be provided at the position of the base end of the outer surface 301 of the sensor element 2.

In the present embodiment, the insulating layer 22 is not provided at a position where the detection electrode section 41 is formed, and the insulating layer 22 is provided at the bottom 32 and on the base end side of the detection electrode section 41. The detection electrode 4A is provided so as to be continuous from the detection electrode section 41 to an outer surface of the insulating layer 22 provided at the bottom 32. This facilitates formation of the electrode 4A. Due to the presence of the insulating layer 22, a bottom electrode section 411 provided on the outer surface of the insulating layer 22 at the bottom 32 does not function as an electrode that conducts oxygen ions ($O^{2-}$).

Figure 6:
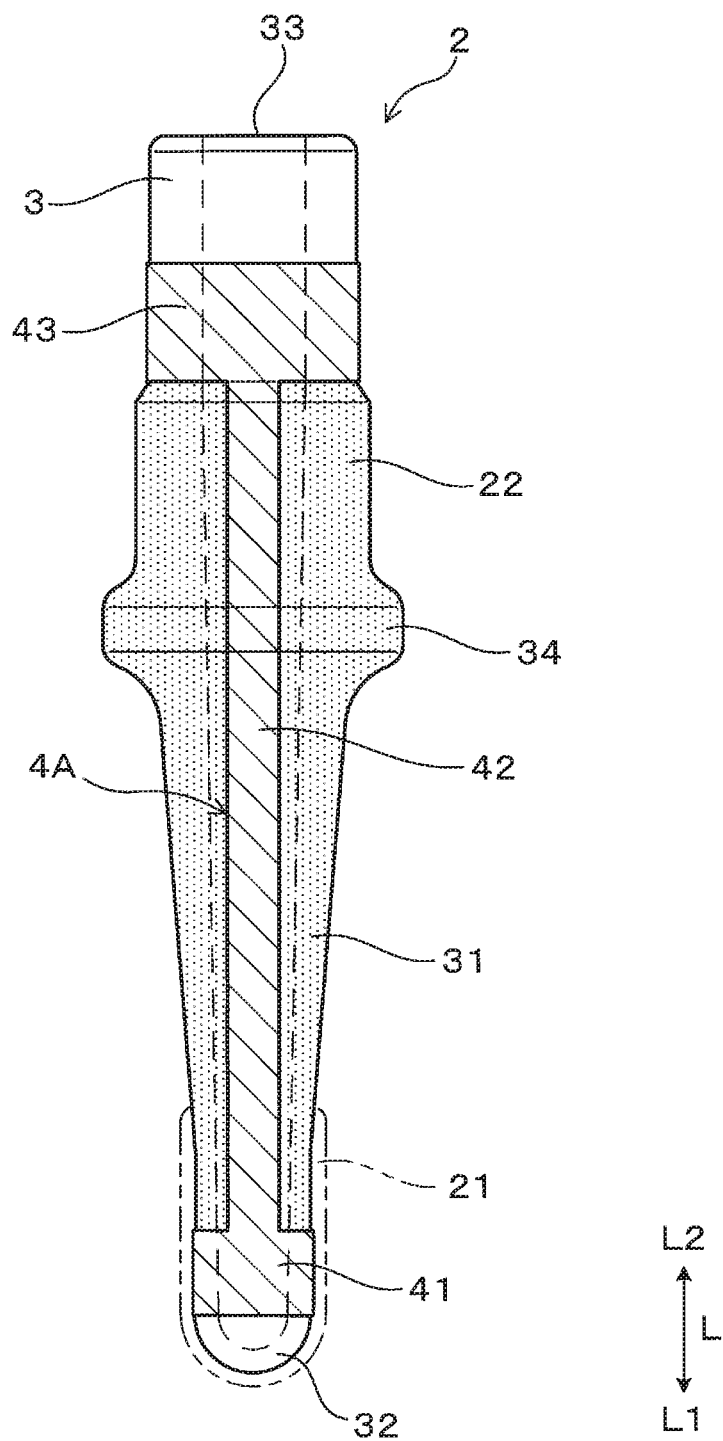
FIG. 6 is an explanatory view showing a formation state of a detection electrode of another sensor element, according to Embodiment 1.
Figure 7:
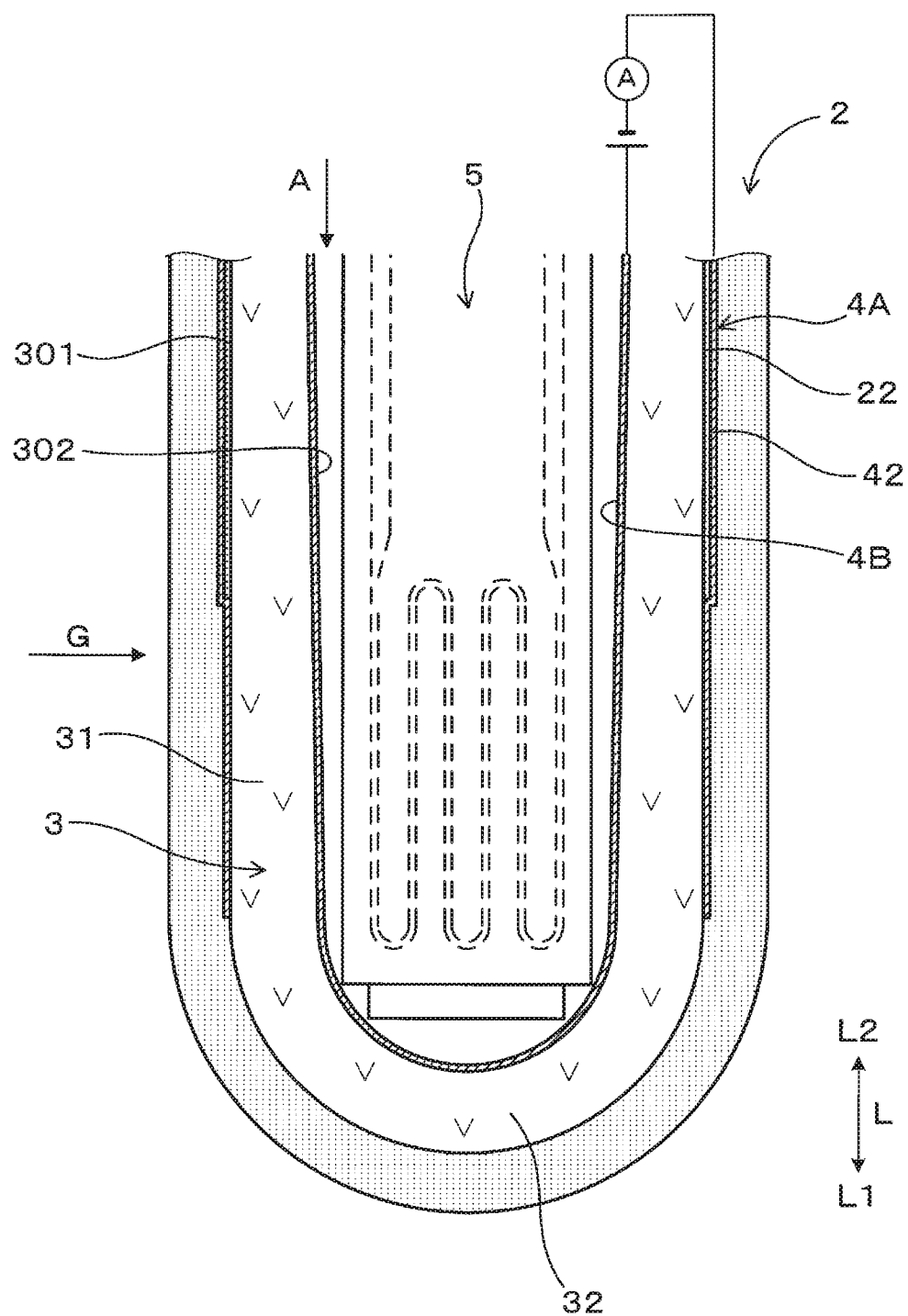
FIG. 7 is an explanatory view showing a cross section of a tip portion of another sensor element, according to Embodiment 1.

As shown in FIG. 6, the attachment electrode section 43 of the detection electrode 4A may be formed on an entire periphery in the circumferential direction C of the solid electrolyte 3. Furthermore, the detection electrode section 41 of the detection electrode 4A does not necessarily formed on the entire periphery in the circumferential direction C of the solid electrolyte 3. As shown in FIGS. 6 and 7, the insulating layer 22 may be provided only on the base end side of the detection electrode section 41 and not provided on the outer surface 301 of the bottom 32.

As shown in FIG. 3, the detection electrode 4A is formed by plating an electrode material on the outer surface 301 of the solid electrolyte 3, and the reference electrode 4B is formed by plating an electrode material on the inner surface 302 of the solid electrolyte 3. The insulating layer 22 is formed by applying an insulating material paste to the outer surface 301 of the solid electrolyte 3 and sintering the paste together with the solid electrolyte 3. When the insulating layer 22 is formed, a portion of the outer surface 301 of the solid electrolyte 3 on which the detection electrode section 41 is to be formed is masked with a tape or the like. Then, by applying the paste to the outer surface 301 of the solid electrolyte 3 with the masked portion and peeling off the tape or the like, the insulating layer 22 is not formed at the masked portion. The insulating layer 22 is composed of an insulating material containing at least one or more of aluminum oxide ($Al_2O_3$), spinel ($MgAl_2O_4$), and insulating glass. The insulating material, which is typically used for the gas sensor 1, has high resistivity and thus has a sufficient insulating effect.

The insulating layer 22 of the present embodiment is formed so that a thickness of an entire portion of the insulating layer 22 is as uniform as possible on the outer surface 301 of the solid electrolyte 3. A portion of the insulating layer 22 located between the tube 31 and the lead electrode section 42 and a portion of the insulating layer 22 located between the tube 31 and the attachment electrode section 43 have a minimum thickness of 4 μm or more. The minimum thickness is a thickness of a portion having a smallest thickness. When the minimum thickness of the insulating layer 22 is less than 4μ, the insulating layer 22 may have an insufficient insulating effect. From the viewpoint of manufacturing, the insulating layer 22 may have, for example, a thickness of 10 μm or less.

(Heater 5)

As shown in FIG. 3, the heater 5 for heating the solid electrolyte 3 is arranged inside the solid electrolyte 3 of the sensor element 2. The heater 5 includes substrates 51A and 51B that are composed of ceramics and a heating element 52 that is provided on the substrate 51B and is constituted by a conductor. A tip portion of the heating element 52 includes a heating section 521 that has a smallest cross-sectional area and generates heat by Joule heat when the heating element 52 is energized.

At the tip portion of the heating element 52, the heating section 521 is formed to have a shape meandering in the axial direction L. The heating section 521 is arranged at a position facing an inner peripheral side of the detection electrode section 41 of the detection electrode 4A and heats the solid electrolyte 3, the reference electrode 4B, and the detection electrode 4A so that the detection electrode section 41 reaches a target temperature. The heater 5 is formed by winding, around the substrate 51A serving as a spindle, the substrate 51B that has a sheet shape and includes the heating element 52.

(Other Configuration of Gas Sensor 1)

As shown in FIG. 1, in addition to the sensor element 2 and the heater 5, the gas sensor 1 includes the housing 61 that holds the sensor element 2, a tip side cover 62 attached to a portion on the tip side L1 of the housing 61, a base end side cover 63 attached to a portion on the base end side L2 of the housing 61, the terminal metal fitting 71 attached to the outer surface 301 of a portion on the base end side L2 of the sensor element 2, the inner terminal metal fitting 72 attached to the inner surface 302 of the portion on the base end side L2 of the sensor element 2, and the like.

(Housing 61)

As shown in FIG. 1, in order to hold the sensor element 2, the housing 61 has an insertion hole 611 that passes through the housing 61 in the axial direction L. The insertion hole 611 has a small-diameter hole portion 612 that is located on the tip side L1 of the axial direction L and a large-diameter hole portion 613 that is located on the base end side L2 of the axial direction L and has a larger diameter than the small-diameter hole portion 612. The sensor element 2 is inserted into the small-diameter hole portion 612 and the large-diameter hole portion 613 of the insertion hole 611, and is held via a sealing material 64, such as talc powder or a sleeve, that is arranged in a space between the sensor element 2 and the large-diameter hole portion 613.

Furthermore, a flange portion 34 which is a portion of the sensor element 2 having a largest outer diameter is fixed to an end of the small-diameter hole portion 612. This prevents the sensor element 2 from protruding from the insertion hole 611 toward the tip side L1. The portion on the base end side L2 in the axial direction L of the housing 61 includes a crimping portion 615 that is bent toward an inner peripheral side. The sealing material 64 is compressed in the axial direction L between the crimping portion 615 and the flange portion 34, and thus the sensor element 2 is held by the housing 61. A portion on the tip side L1 of the sensor element 2, in particular, a portion on the tip side L1 of the sensor element 2 including the detection electrode section 41 and the lead electrode section 42 is arranged to protrude from the housing 61 toward the tip side L1 of the axial direction L.

(Tip Side Cover 62 and Base End Side Cover 63)

As shown in FIG. 1, the tip side cover 62 for protecting the sensor element 2 by covering the portion of the sensor element 2 protruding from the housing 61 toward the tip side L1 is attached to the portion on the tip side L1 in the axial direction L of the housing 61. The tip side cover 62 is arranged in the exhaust pipe 81. The tip side cover 62 has a gas passage hole 621 through which the detection gas G passes. The tip side cover 62 may have a double structure or a single structure. The exhaust gas as the detection gas G flowing from the gas passage hole 621 of the tip side cover 62 into an inside of the tip side cover 62 passes through the protective layer 21 of the sensor element 2 and is guided to the detection electrode 4A.

The base end side cover 63 is attached to the portion on the base end side L2 in the axial direction L of the housing 61. The base end side cover 63 is arranged outside the exhaust pipe 81. A portion of the base end side cover 63 has an introduction hole 631 for introducing air as the reference gas A into an inside of the base end side cover 63. At the introduction hole 631, a filter 632 that does not allow liquid to pass through but allows gas to pass through is arranged. The reference gas A introduced from the introduction hole 631 into the inside of the base end side cover 63 passes through a space inside the base end side cover 63 and is guided to the reference electrode 4B on the inner surface 302 of the sensor element 2.

As shown in FIG. 1, the terminal metal fitting 71 in contact with the attachment electrode section 43 of the detection electrode 4A is attached to the outer surface 301 of the portion on the base end side L2 of the sensor element 2. Furthermore, the inner terminal metal fitting 72 in contact with the portion on the base end side L2 of the reference electrode 4B is attached to the inner surface 302 of the portion on the base end side L2 of the sensor element 2. To the terminal metal fitting 71 and the inner terminal metal fitting 72, a lead wire 65 for electrically connecting the detection electrode 4A and the reference electrode 4B of the sensor element 2 to the external control unit 10 is attached. The lead wire 65 is held by a bush 66 arranged inside the base end side cover 63.

(Effects)

In the gas sensor 1 of the present embodiment, the insulating layer 22 is provided not only between the lead electrode section 42 of the detection electrode 4A and the tube 31 of the solid electrolyte 3 but also between the attachment electrode section 43 of the detection electrode 4A to which the terminal metal fitting 71 is attached and the tube 31 of the solid electrolyte 3. Thus, when the portion on the base end side L2 of the sensor element 2 is heated to a high temperature of 400° C. or more, it is possible to prevent a leakage current from being generated between the attachment electrode section 43 of the detection electrode 4A and the reference electrode 4B.

Accordingly, in a case where the gas sensor 1 is used as the air-fuel ratio sensor, even when the portion on the base end side L2 of the sensor element 2 is exposed to a high temperature environment of 400° C. or more, it is possible to prevent an offset current from being included in an output current as the sensor output at an air-fuel ratio close to the theoretical air-fuel ratio. Furthermore, in a case where the gas sensor 1 is used as the oxygen sensor, even when the portion on the base end side L2 of the sensor element 2 is exposed to a high temperature environment of 400° C. or more, it is possible to prevent an error voltage from being included in an output voltage as the sensor output.

In the sensor element 2 including the solid electrolyte 3 having a bottomed tubular shape, when the exhaust gas has reached a high temperature, an entire portion of the sensor element 2 tends to reach a high temperature. It has been found that, in this case, a minute leakage current flows between the reference electrode 4B and the detection electrode 4A. In a conventional gas sensor 1, an influence of the minute leakage current on detection accuracy of the gas sensor 1 has not been regarded as a serious problem. From the viewpoint of promoting a reduction in emissions and low fuel consumption in recent years, however, the influence of the minute leakage current on the detection accuracy of the gas sensor 1, in particular, a shift of a stoichiometric point (a point at which the air-fuel ratio of the exhaust gas is detected to be the theoretical air-fuel ratio) caused by the minute electric current has come to be regarded as a problem. The gas sensor 1 of the present embodiment solves such a new problem that has arisen in recent years.

The insulating layer 22 of the present embodiment is provided in order not only to reduce variations in the sensor output of the gas sensor 1 by defining the area of the region in which the detection electrode section 41 is formed but also to eliminate a leakage current caused by movement of oxygen in the reference gas A such as air through the solid electrolyte 3.

In the gas sensor 1, the solid electrolyte 3 at the portion on the tip side L1 of the sensor element 2 including the detection electrode section 41 of the detection electrode 4A is heated to a temperature at which oxygen ionic conduction is activated. In many cases, the portion on the base end side L2 of the sensor element 2 is not heated to the temperature at which the solid electrolyte 3 is activated.

Depending on a combustion process in the internal combustion engine 8, however, in some cases, the exhaust gas reaches a high temperature, and the solid electrolyte 3 at the portion on the base end side L2 of the sensor element 2 is heated to the temperature at which the solid electrolyte 3 is activated. In this case, oxygen in the reference gas A that is present around the detection electrode 4A and the reference electrode 4B may be ionized and pass through the solid electrolyte 3 from the detection electrode 4A to the reference electrode 4B. Thus, at the portion on the base end side L2 of the solid electrolyte 3 that the exhaust gas as the detection gas G does not reach, oxygen ions are conducted and accordingly an electric current is generated. The electric current is not an electric current flowing due to a change in composition of the detection gas G, but is a leakage current that causes an error in detection of the air-fuel ratio or the like.

When the gas sensor 1 is used as the air-fuel ratio sensor, due to a voltage applied between the detection electrode 4A and the reference electrode 4B so that the reference electrode 4B is on the positive side, ionized oxygen may pass through the solid electrolyte 3 from the detection electrode 4A to the reference electrode 4B, and this may cause a leakage current. When the gas sensor 1 is used as the oxygen sensor, due to a slight difference between oxygen concentration of the reference gas A in contact with the detection electrode 4A and the terminal metal fitting 71 and oxygen concentration of the reference gas A in contact with the reference electrode 4B and the inner terminal metal fitting 72, ionized oxygen may pass through the solid electrolyte 3, and this may cause a leakage current.

In the gas sensor 1 of the present embodiment, the arrangement of the insulating layer 22 can prevent generation of such a leakage current. Therefore, the gas sensor 1 of the present embodiment can improve accuracy of gas detection by preventing a leakage current from being generated between the attachment electrode section 43 of the detection electrode 4A and the reference electrode 4B.

Embodiment 2

In the sensor element 2 of the present embodiment, an ingenious method has been employed to form the insulating layer 22 provided between the tube 31 of the solid electrolyte and each of the lead electrode section 42 and the attachment electrode section 43 of the detection electrode 4A.

Figure 9:
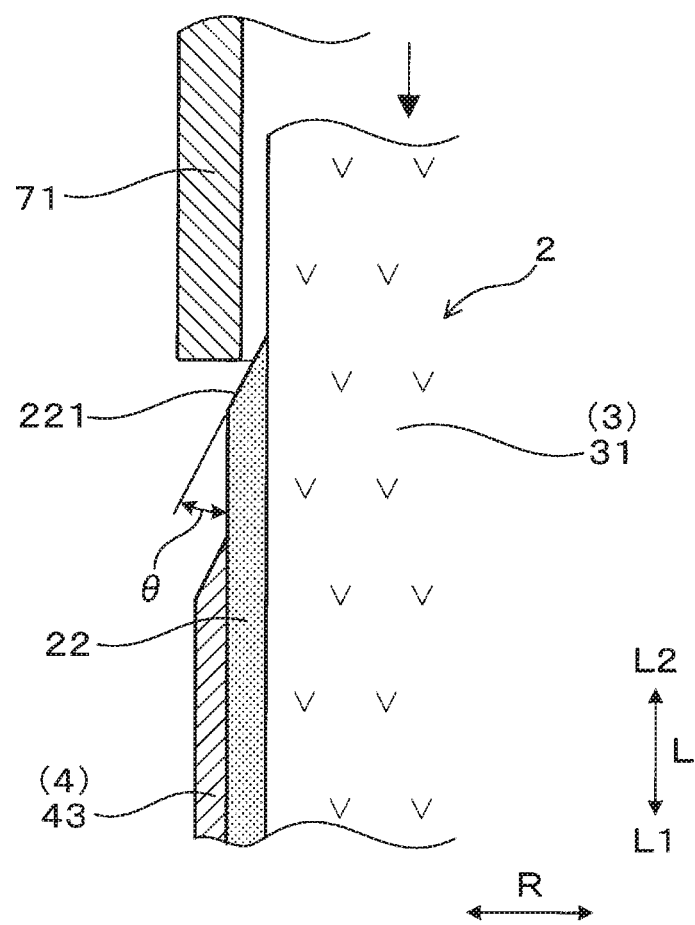
FIG. 9 is an explanatory view showing an enlarged part of a cross section of the terminal metal fitting to be attached to the sensor element, according to Embodiment 2.

As shown in FIGS. 8 and 9, an end on the base end side L2 of the axial direction L of the insulating layer 22 is provided on the base end side L2 of an end on the base end side L2 of the axial direction L of the attachment electrode section 43. The end on the base end side L2 of the insulating layer 22 constitutes an outermost portion of the outer surface 301 of the tube 31 and is exposed on the outer surface 301 of the tube 31. Furthermore, the end on the base end side L2 of the insulating layer 22 has a tapered surface 221 whose thickness in the radial direction R from the center axis O is reduced toward the base end side L2 of the tube 31. The tapered surface 221 is a surface by which the terminal metal fitting 71 attached to the outer periphery of the tube 31 is guided from the base end side L2 toward the tip side L1 of the tube 31 during attachment of the terminal metal fitting 71. A general portion of the insulating layer 22 except the end on the base end side L2 of the insulating layer 22 is provided on the outer surface 301 of the solid electrolyte 3 to have a uniform thickness.

In the present embodiment, when the terminal metal fitting 71 is attached to the solid electrolyte 3, the terminal metal fitting 71 can be brought into contact with the tapered surface 221 at the end on the base end side L2 of the insulating layer 22. Then, the terminal metal fitting 71 can be slid on the tapered surface 221. Thus, even when the terminal metal fitting 71 is brought into contact with the end on the base end side L2 of the insulating layer 22, peeling, chipping, or the like is less likely to occur at the end on the base end side L2 of the insulating layer 22.

In the present embodiment, an entire portion of the tapered surface 221 at the end on the base end side L2 of the insulating layer 22 is exposed. Alternatively, the attachment electrode section 43 may be provided on a portion on the tip side L1 of the tapered surface 221. In this case, only a portion on the base end side L2 of the tapered surface 221 is exposed. The tapered surface 221 constitutes the outermost portion of the outer surface 301 of the tube 31, and thus is a surface in contact with the terminal metal fitting 71 when the terminal metal fitting 71 is attached to the solid electrolyte 3.

As shown in FIG. 9, the tapered surface 221 has an inclination angle θ of 60° or less with respect to the axial direction L parallel to the center axis O. When the inclination angle θ of the tapered surface 221 exceeds 60°, peeling, chipping, or the like may occur at the end on the base end side L2 of the insulating layer 22. When the inclination angle θ of the tapered surface 221 is reduced, a length in the axial direction L of the end on the base end side L2 of the insulating layer 22 is increased. From the viewpoint of manufacturing, therefore, the tapered surface 221 may have, for example, an inclination angle θ of 15° or more.

Instead of forming the tapered surface 221 at the end on the base end side L2 of the insulating layer 22, a curved surface may be formed at a corner portion on the base end side L2 of the insulating layer 22. Also in this case, peeling, chipping, or the like is less likely to occur in the insulating layer 22.

Other configuration, effects, and the like of the gas sensor 1 of the present embodiment are the same as those of Embodiment 1. Also in the present embodiment, components indicated by the same reference signs as Embodiment 1 are the same as those of Embodiment 1.

Embodiment 3

Also in the sensor element 2 of the present embodiment, an ingenious method has been employed to form the insulating layer 22 provided between the tube 31 of the solid electrolyte and each of the lead electrode section 42 and the attachment electrode section 43 of the detection electrode 4A.

Figure 10:
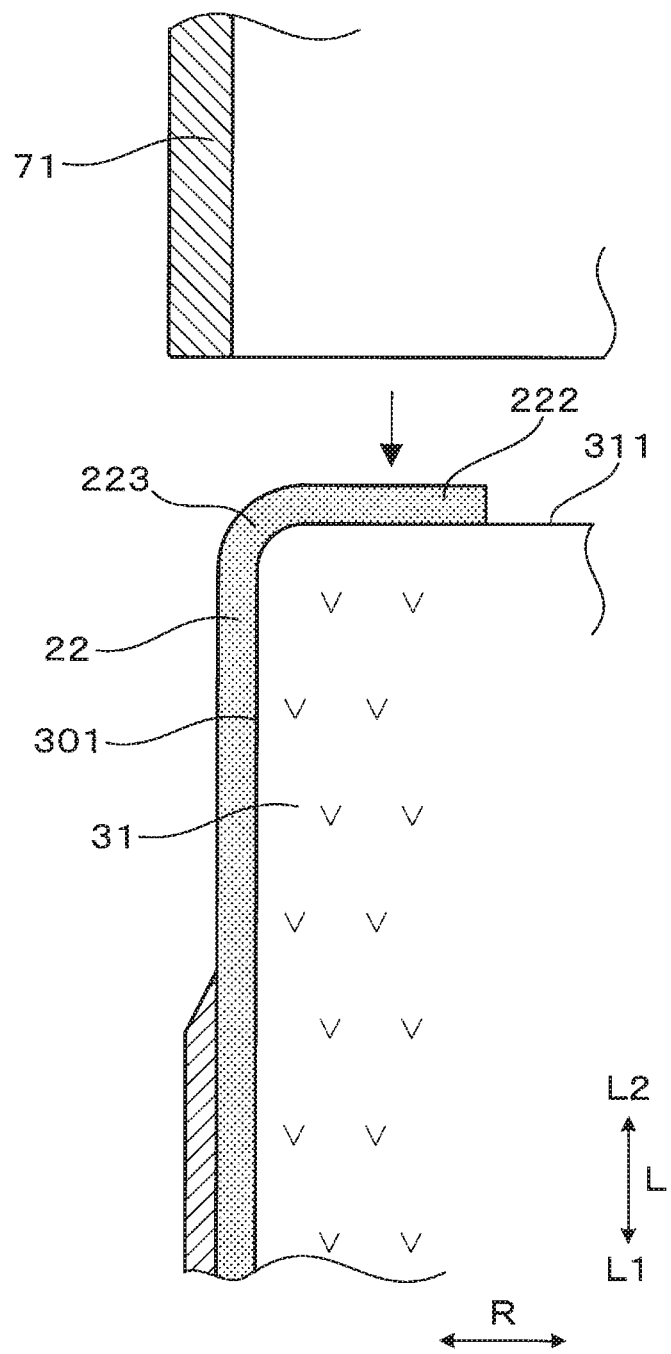
FIG. 10 is an explanatory view showing an enlarged part of a cross section of the terminal metal fitting to be attached to the sensor element, according to Embodiment 3.

As shown in FIG. 10, an end 222 on the base end side L2 of the axial direction L of the insulating layer 22 of the present embodiment is provided so as to be continuous from the outer surface 301 of the tube 31 to an end surface 311 on the base end side L2 of the tube 31. A corner portion 223 of the insulating layer 22 located at a corner portion on the base end side L2 of the tube 31 preferably has a curved surface or the like. The end 222 of the insulating layer 22 does not need to be provided on an entire portion of the end surface 311 on the base end side L2 of the tube 31. The end 222 of the insulating layer 22 is provided at an outer peripheral side position on the end surface 311 on the base end side L2 of the tube 31, but is not provided at a center side position on the end surface 311 on the base end side L2 of the tube 31.

By a roll transfer method, when an insulating material paste for forming the insulating layer 22 is applied to the outer surface 301 of the tube 31 of the solid electrolyte 3, the paste can also be applied to the end surface 311 on the base end side L2 of the tube 31. Subsequently, by sintering the paste together with the solid electrolyte 3, the insulating layer 22 can be formed from the paste.

Similarly to Embodiment 2, also in the present embodiment, even when the terminal metal fitting 71 is brought into contact with the corner portion 223 on the base end side L2 of the insulating layer 22, peeling, chipping, or the like is less likely to occur at the corner portion 223 on the base end side L2. Other configuration, effects, and the like of the gas sensor 1 of the present embodiment are the same as those of Embodiment 1. Also in the present embodiment, components indicated by the same reference signs as Embodiment 1 are the same as those of Embodiment 1.

The present disclosure is not limited only to the above embodiments, and can further constitute different embodiments without departing from the scope of the present disclosure.

<Confirmation Test 1>

Figure 11:
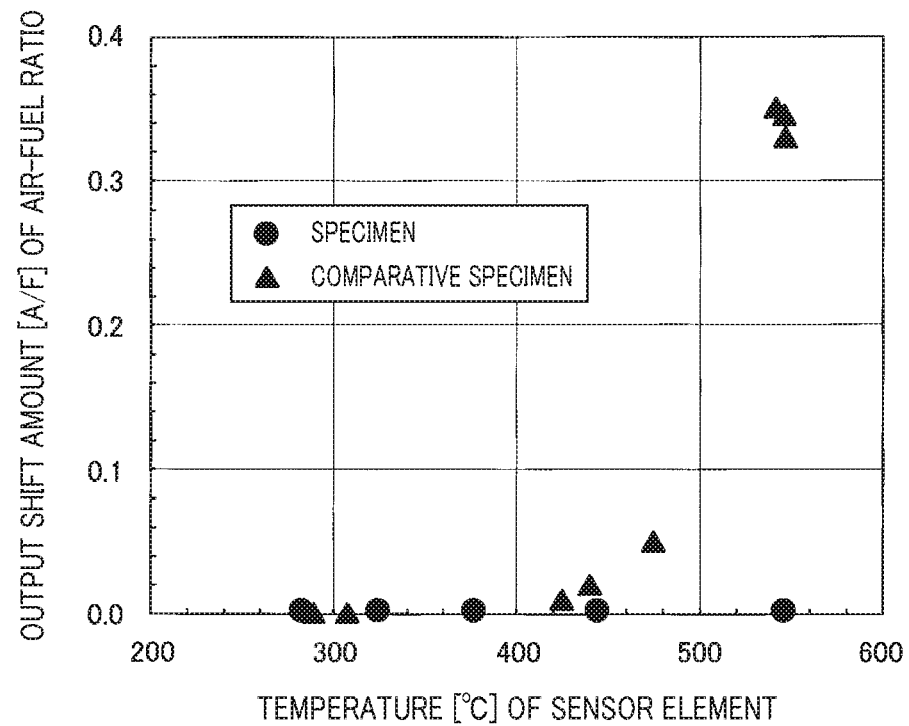
FIG. 11 is a graph showing a relationship between a temperature of the sensor element and an output shift amount of air-fuel ratio, according to Confirmation Test 1.

A test was performed to determine a relationship between a temperature of the sensor element 2 and an error occurring in the sensor output of the gas sensor 1 used as the air-fuel ratio sensor, for the gas sensor 1 (specimen) of Embodiment 1 in which the insulating layer 22 was included in the sensor element 2 and a gas sensor (comparative specimen) in which the insulating layer 22 was not included in the sensor element 2. FIG. 11 shows an error that occurred in the sensor output of the gas sensor 1 when the temperature [° C.] of the sensor element 2 was varied as appropriate.

Since the gas sensor 1 of Embodiment 1 was used as the air-fuel ratio sensor, the error occurring in the sensor output was measured as an output shift amount [A/F] (an amount of change in air-fuel ratio) indicating an offset amount from a detection value of the air-fuel ratio. The output shift amount is, for example, an amount of error that occurs when a detection value of the air-fuel ratio supposed to be 14.7, which is the theoretical air-fuel ratio, is a value slightly larger than 14.7. The temperature of the sensor element 2 was set to an average temperature from the portion on the tip side L1 to the portion on the base end side L2 of the axial direction L of the sensor element 2. Furthermore, a thickness of the general portion of the insulating layer 22 was set to 10 μm.

As shown in FIG. 11, it was found that in the gas sensor 1 of the specimen, when the temperature of the sensor element 2 was in the high temperature range of approximately 280° C. or more to approximately 540° C. or less, the output shift amount of the sensor output was almost 0 (zero). On the other hand, it was found that in the gas sensor of the comparative specimen, when the temperature of the sensor element 2 was approximately 420° C. or more, the output shift amount was detected, and as the temperature of the sensor element 2 rose, the output shift amount was increased. The results showed that the gas sensor 1 for detecting an air-fuel ratio of Embodiment 1 reduced a leakage current generated between the reference electrode 4B and the detection electrode 4A of the sensor element 2 so that almost no offset error due to the leakage current occurred in the sensor output.

<Confirmation Test 2>

Figure 12:
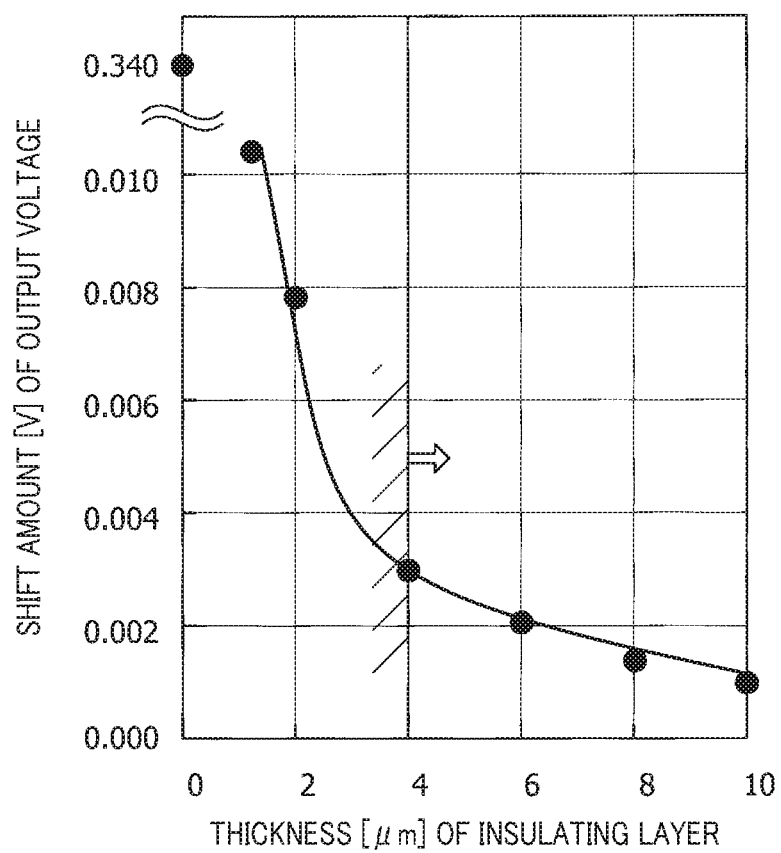
FIG. 12 is a graph showing a relationship between a thickness of an insulating layer and an output shift amount of air-fuel ratio, according to Confirmation Test 2.

A test was performed to determine a relationship between a thickness of the insulating layer 22 provided on the outer surface 301 of the tube 31 of the solid electrolyte 3 and an error occurring in the sensor output of the gas sensor 1. FIG. 12 shows an error that occurred in the sensor output of the gas sensor 1 of Embodiment 1 when the thickness [µm] of the insulating layer 22 was varied as appropriate. Since the gas sensor 1 of Embodiment 1 was used as the air-fuel ratio sensor, the error occurring in the sensor output was measured as an output shift amount [A/F] (an amount of change in air-fuel ratio) indicating an offset amount from a detection value of the air-fuel ratio.

The thickness of the insulating layer 22 was set to an average thickness of the general portion of the insulating layer 22 except the end on the base end side L2 of the insulating layer 22 at which the tapered surface 221 was formed. The thickness of the insulating layer 22 was a minimum thickness of the portion of the insulating layer 22 located between the tube 31 and the lead electrode section 42 and the portion of the insulating layer 22 located between the tube 31 and the attachment electrode section 43. The temperature of the sensor element 2, which was the average temperature from the portion on the tip side L1 to the portion on the base end side L2 of the axial direction L of the sensor element 2, was set to 550° C.

As shown in FIG. 12, it was found that as the thickness of the insulating layer 22 was reduced, the output shift amount of the sensor output was increased. Furthermore, it was found that when the thickness of the insulating layer 22 became less than 4 µm, the output shift amount was suddenly increased. This is presumably because when the thickness of the insulating layer 22 was less than 4 µm, among projections and recesses formed on the surface of the solid electrolyte 3, the projections appeared on the surface of the insulating layer 22 and prevented the insulating layer 22 from sufficiently insulating the solid electrolyte 3 from the attachment electrode section 43 of the detection electrode 4A. In order to obtain a sufficient insulating effect of the insulating layer 22, therefore, the insulating layer 22 preferably has a minimum thickness of 4 µm or more.

<Confirmation Test 3>

Figure 13:
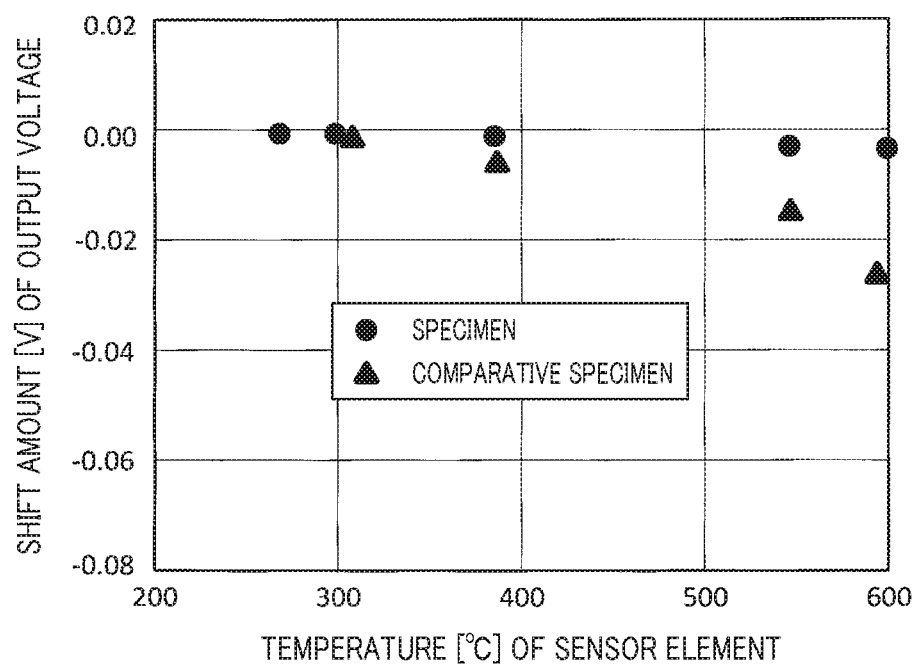
FIG. 13 is a graph showing a relationship between a temperature of the sensor element and a shift amount of output voltage, according to Confirmation Test 3.

A test was performed to determine a relationship between a temperature of the sensor element 2 and an error occurring in the sensor output of the gas sensor 1 used as the oxygen sensor, for the gas sensor 1 (specimen) of Embodiment 1 in which the insulating layer 22 was included in the sensor element 2 and the gas sensor (comparative specimen) in which the insulating layer 22 was not included in the sensor element 2. FIG. 13 shows an error that occurred in the sensor output of the gas sensor 1 when the temperature of the sensor element 2 was varied as appropriate.

The error occurring in the sensor output was measured as a change in output voltage (electromotive force) of the gas sensor 1 in which the air-fuel ratio of the detection gas G was the theoretical air-fuel ratio, when the temperature of the sensor element 2 was varied, and the change in the output voltage of the gas sensor 1 was indicated by a shift amount [V] of the output voltage. The temperature of the sensor element 2 was set to an average temperature from the portion on the tip side L1 to the portion on the base end side L2 of the axial direction L of the sensor element 2. Furthermore, a thickness of the general portion of the insulating layer 22 was set to 10 µm.

As shown in FIG. 13, it was found that in the gas sensor 1 of the specimen, when the temperature of the sensor element 2 was in the high temperature range of approximately 270° C. or more to approximately 600° C. or less, the shift amount of the output voltage was almost close to 0 (zero). On the other hand, it was found that in the gas sensor of the comparative specimen, when the temperature of the sensor element 2 was approximately 380° C. or more, the shift amount of the output voltage was detected, and as the temperature of the sensor element 2 rose, the shift amount of the output voltage was increased. The results showed that the gas sensor 1 for detecting oxygen concentration of Embodiment 1 reduced a leakage current generated between the reference electrode 4B and the detection electrode 4A of the sensor element 2 so that almost no offset error due to the leakage current occurred in the sensor output.

<Confirmation Test 4>

Figure 14:
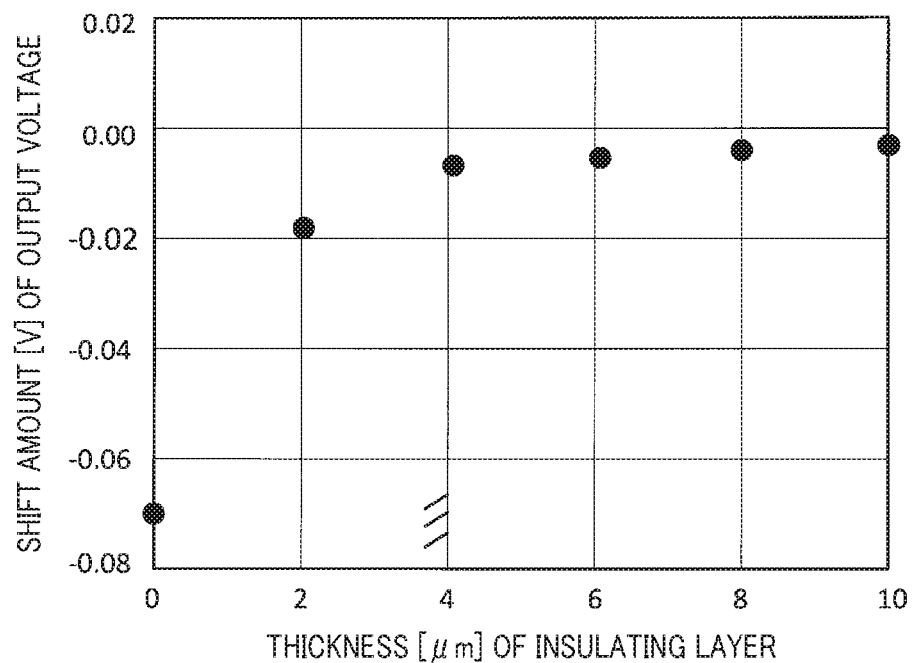
FIG. 14 is a graph showing a relationship between a thickness of the insulating layer and a shift amount of output voltage, according to Confirmation Test 4.

A test was performed to determine a relationship between a thickness of the insulating layer 22 provided on the outer surface 301 of the tube 31 of the solid electrolyte 3 and an error occurring in the sensor output of the gas sensor 1 used as the oxygen sensor. FIG. 14 shows an error that occurred in the sensor output of the gas sensor 1 of Embodiment 1 when the thickness [µm] of the insulating layer 22 was varied as appropriate. The error occurring in the sensor output was measured as a change in output voltage (electromotive force) of the gas sensor 1 in which the air-fuel ratio of the detection gas G was the theoretical air-fuel ratio, when the thickness of the insulating layer 22 was varied, and the change in the output voltage of the gas sensor 1 was indicated by a shift amount [V] of the output voltage. The thickness of the insulating layer 22 and the temperature of the sensor element 2 were the same as those of Confirmation Test 2.

As shown in FIG. 14, it was found that as the thickness of the insulating layer 22 was reduced, the shift amount of the output voltage was increased. Furthermore, it was found that when the thickness of the insulating layer 22 became less than 4 µm, the shift amount was suddenly increased. This is presumably because when the thickness of the insulating layer 22 was less than 4 µm, among the projections and recesses formed on the surface of the solid electrolyte 3, the projections appeared on the surface of the insulating layer 22 and prevented the insulating layer 22 from sufficiently insulating the solid electrolyte 3 from the attachment electrode section 43 of the detection electrode 4A. In order to obtain a sufficient insulating effect of the insulating layer 22, therefore, the insulating layer 22 preferably has a minimum thickness of 4 µm or more.

<Confirmation Test 5>

A test was performed to determine, for the gas sensor 1 of Embodiment 2, a relationship between the inclination angle θ of the tapered surface 221 at the end on the base end side L2 of the insulating layer 22 and the number of occurrences of defects such as peeling or chipping in the insulating layer 22. The number of occurrences of defects was counted when peeling or chipping occurred in the insulating layer 22 while the terminal metal fitting 71 was attached to the outer surface 301 of the solid electrolyte 3. For each inclination angle θ, the insulating layer 22 was checked 20 times for the occurrence of peeling or chipping.

Figure 15:
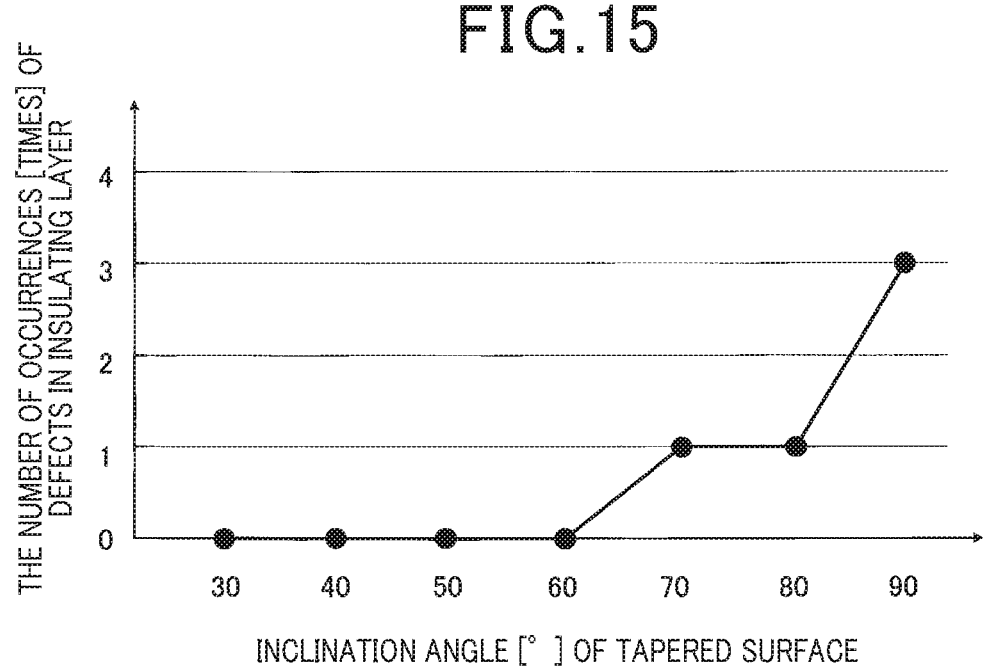
FIG. 15 is a graph showing a relationship between an inclination angle of a tapered surface and the number of occurrences of defects in the insulating layer, according to Confirmation Test 5.

As shown in FIG. 15, it was found that when the inclination angle θ of the tapered surface 221 was 60° or less, no peeling or chipping occurred in the insulating layer 22. On the other hand, it was found that when the inclination angle θ of the tapered surface 221 exceeded 60°, peeling or chipping occurred several times. The results showed that by setting the inclination angle θ of the tapered surface 221 to 60° or less, the insulating layer 22 was protected while the terminal metal fitting 71 was assembled to the sensor element 2.

What is claimed is:

1. A gas sensor comprising a sensor element, wherein:
the sensor element includes
a solid electrolyte that has a bottomed tubular shape and in which a tip portion of a tube having a tubular shape thereof is blocked by a bottom having a curved surface,
a detection electrode that is provided at least on an outer surface of the tube and is exposed to detection gas guided to an outside of the solid electrolyte, and
a reference electrode that is provided at least on an inner surface of the tube and is exposed to reference gas guided to an inside of the solid electrolyte;
the detection electrode includes
a detection electrode area that is provided on an entire periphery or a part in a circumferential direction around a center axis of the tube at a position on a tip side of an axial direction along the center axis,
an attachment electrode area that is provided on an entire periphery or a part in the circumferential direction of the tube at a position on a base end side of the axial direction and is in contact with a terminal metal fitting attached to an outer periphery of the tube,
a lead electrode area that is provided on a part in the circumferential direction of the tube at a position where the detection electrode area is connected to the attachment electrode area and that is formed in a formation region in the circumferential direction smaller than a formation region in the circumferential direction of the attachment electrode area; and
a bottom electrode area;
an insulating layer that insulates the solid electrolyte from the attachment electrode area and the lead electrode area is provided between the tube of the solid electrolyte and each of the attachment electrode area and the lead electrode area;
in the detection electrode, the insulating layer is not provided at a position where the detection electrode area is formed, and the insulating layer is provided at the bottom;
the bottom electrode area is provided on an outer surface of the insulating layer at the bottom; and
the tube has a part where the outer surface of the tube is exposed, at the end of the base end side of the axial direction.

2. The gas sensor according to claim 1, wherein:
the gas sensor is configured to communicate to an electromotive force detection circuit; and
on the basis of a difference in oxygen concentration between the reference gas in contact with the reference electrode and the detection gas in contact with the detection electrode, the gas sensor is configured to detect by the electromotive force detection circuit, an electromotive force generated between the detection electrode and the reference electrode through the solid electrolyte.

3. The gas sensor according to claim 1, wherein:
a diffusion resistance layer that covers at least an entire portion of the detection electrode area of the detection electrode and limits diffusion of the detection gas is provided on the outer surface of the tube of the solid electrolyte;
the gas sensor is configured to communicate to a current detection circuit and a voltage application circuit; and
while a voltage is applied, by the voltage application circuit, between the detection electrode and the reference electrode, the gas sensor is configured to detect, by the current detection circuit, a limiting current generated between the detection electrode and the reference electrode through the solid electrolyte.

4. The gas sensor according to claim 1, wherein a portion of the insulating layer located between the tube and each of the attachment electrode area and the lead electrode area has a minimum thickness of 4 µm or more.

5. The gas sensor according to claim 1, wherein:
the solid electrolyte contains zirconia;
the reference electrode and the detection electrode contain noble metal; and
the insulating layer contains at least one or more of aluminum oxide, spinel, and insulating glass.

6. The gas sensor according to claim 1, wherein:
the gas sensor is arranged in an exhaust pipe of an internal combustion engine in which exhaust gas as the detection gas flows;
a single catalyst or a plurality of catalysts arranged in a direction of flow of the exhaust gas are arranged in the exhaust pipe; and
the gas sensor is arranged at a position on a downstream side of the flow of the exhaust gas from the at least one catalyst in the exhaust pipe.

7. The gas sensor according to claim 1, wherein:
the gas sensor is configured to communicate to an electromotive force detection circuit; and
the gas sensor is configured to is configured to detect, by the electromotive force detection circuit, an electromotive force generated between the detection electrode and the reference electrode through the solid electrolyte based on a difference in oxygen concentration between the reference gas in contact with the reference electrode and the detection gas in contact with the detection electrode.

8. The gas sensor according to claim 1, wherein:
a diffusion resistance layer that covers at least an entire portion of the detection electrode area of the detection electrode and limits diffusion of the detection gas is provided on the outer surface of the tube of the solid electrolyte;
the gas sensor is configured to communicate to a current detection circuit; and
the gas sensor is configured to is configured to detect, by the current detection circuit, a limiting current generated between the detection electrode and the reference electrode through the solid electrolyte.

9. A gas sensor comprising a sensor element, wherein:
the sensor element includes
a solid electrolyte that has a bottomed tubular shape and in which a tip portion of a tube having a tubular shape thereof is blocked by a bottom having a curved surface,
a detection electrode that is provided at least on an outer surface of the tube and is exposed to detection gas guided to an outside of the solid electrolyte, and
a reference electrode that is provided at least on an inner surface of the tube and is exposed to reference gas guided to an inside of the solid electrolyte;
the detection electrode includes a detection electrode area that is provided on an entire periphery or a part in a circumferential direction around a center axis of the tube at a position on a tip side of an axial direction along the center axis, an attachment electrode area that is provided on an entire periphery or a part in the circumferential direction of the tube at a position on a base end side of the axial direction and is in contact with a terminal metal fitting attached to an outer periphery of the tube, a lead electrode area that is provided on a part in the circumferential direction of the tube at a position where the detection electrode area is connected to the attachment electrode area and that is formed in a formation region in the circumferential direction smaller than a formation region in the circumferential direction of the attachment electrode area; and a bottom electrode area;

an insulating layer that insulates the solid electrolyte from the attachment electrode area and the lead electrode area is provided between the tube of the solid electrolyte and each of the attachment electrode area and the lead electrode area;

in the detection electrode, the insulating layer is not provided at a position where the detection electrode area is formed, and the insulating layer is provided at the bottom;

the bottom electrode area is provided on an outer surface of the insulating layer at the bottom;

an end on the base end side of the axial direction of the insulating layer is provided on the base end side of an end on the base end side of the axial direction of the attachment electrode area, is exposed on the outer surface of the tube, and has a tapered surface; and a thickness in a radial direction from the center axis of the tapered surface is reduced toward the base end side of the axial direction of the tube so that the terminal metal fitting attached to the outer periphery of the tube is guided from the base end side toward the tip side of the axial direction of the tube.

10. The gas sensor according to claim 9, wherein an inclination angle of the tapered surface with respect to the center axis is 60° or less.

11. A gas sensor comprising a sensor element, wherein:
the sensor element includes a solid electrolyte that has a bottomed tubular shape and in which a tip portion of a tube having a tubular shape thereof is blocked by a bottom having a curved surface, a detection electrode that is provided at least on an outer surface of the tube and is exposed to detection gas guided to an outside of the solid electrolyte, and a reference electrode that is provided at least on an inner surface of the tube and is exposed to reference gas guided to an inside of the solid electrolyte;

the detection electrode includes a detection electrode area that is provided on an entire periphery or a part in a circumferential direction around a center axis of the tube at a position on a tip side of an axial direction along the center axis, an attachment electrode area that is provided on an entire periphery or a part in the circumferential direction of the tube at a position on a base end side of the axial direction and is in contact with a terminal metal fitting attached to an outer periphery of the tube, a lead electrode area that is provided on a part in the circumferential direction of the tube at a position where the detection electrode area is connected to the attachment electrode area and that is formed in a formation region in the circumferential direction smaller than a formation region in the circumferential direction of the attachment electrode area; and a bottom electrode area;

an insulating layer that insulates the solid electrolyte from the attachment electrode area and the lead electrode area is provided between the tube of the solid electrolyte and each of the attachment electrode area and the lead electrode area;

in the detection electrode, the insulating layer is not provided at a position where the detection electrode area is formed, and the insulating layer is provided at the bottom;

the bottom electrode area is provided on an outer surface of the insulating layer at the bottom;

an end on the base end side of the axial direction of the insulating layer is provided so as to be continuous from the outer surface of the tube to an end surface on the base end side of the tube; and a corner portion of the insulating layer located at a corner portion on the base end side of the tube has a curved surface.

\* \* \* \* \*